United States Patent [19]
Mathes

[11] 3,938,516
[45] Feb. 17, 1976

[54] INHALATION DEVICE

[75] Inventor: Stanley Mathes, Mountain View, Calif.

[73] Assignee: Syntex Puerto Rico, Inc., Humacao, P.R.

[22] Filed: Jan. 13, 1975

[21] Appl. No.: 540,917

[52] U.S. Cl. ................ 128/266; 128/206; 128/208
[51] Int. Cl.² ........................................ A61M 13/00
[58] Field of Search .......... 128/206, 207, 208, 266; 222/193

[56] References Cited
UNITED STATES PATENTS

| | | | |
|---|---|---|---|
| 2,517,482 | 8/1950 | Hall | 128/206 |
| 2,672,865 | 3/1954 | Willis | 128/206 |
| 3,807,400 | 4/1974 | Cocozza | 128/266 |
| 3,858,583 | 1/1975 | Hallworth | 128/266 |

*Primary Examiner*—Aldrich F. Medbery
*Attorney, Agent, or Firm*—Joseph I. Hirsch; William B. Walker

[57] ABSTRACT

An inhalation device having an elongate housing having one or more passageways for the passage of air therethrough. Each passageway, of relatively small diameter, opens into an emptying chamber, of relatively greater diameter, adjacent that end of the housing which is adapted for insertion into the mouth or nose of a user. Adjacent that end of the emptying chamber closest to the passageway(s), the housing has means for receiving or presenting a unit dose of powdered medicament for administration. During inhalation, the air stream passing over and directed into the powdered medicament holder entrains the powdered medicament which is then carried into the nose, throat or lungs of the user where beneficial or therapeutic action of the medicament occurs.

28 Claims, 6 Drawing Figures

U.S. Patent  Feb 17, 1976  Sheet 1 of 2  3,938,516
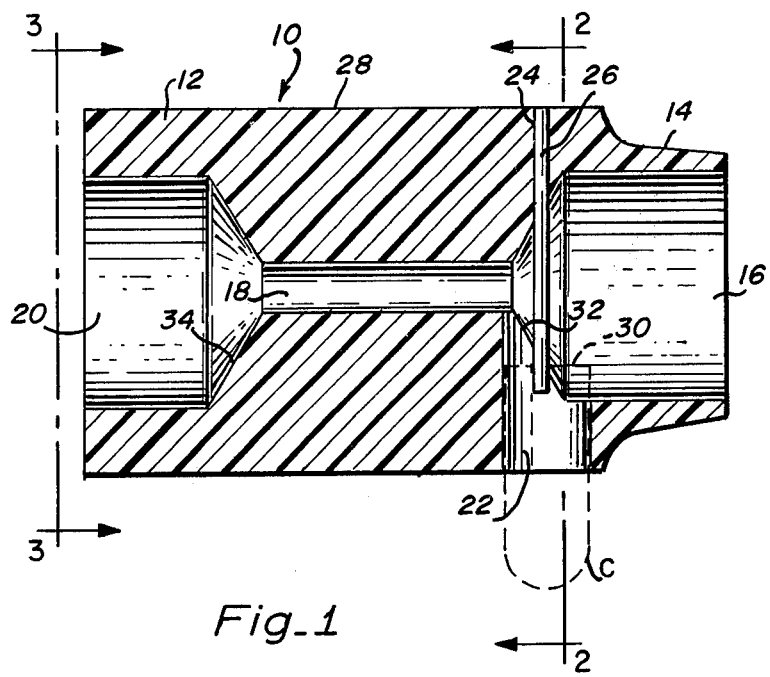
Fig_1
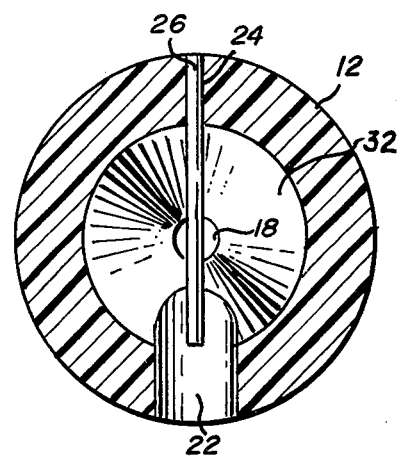
Fig_2
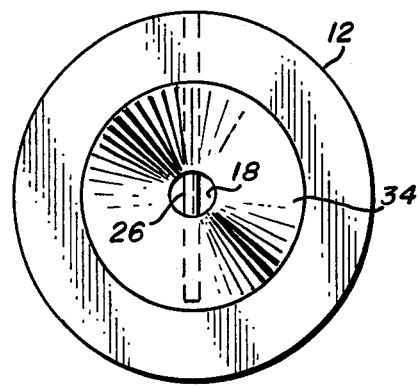
Fig_3

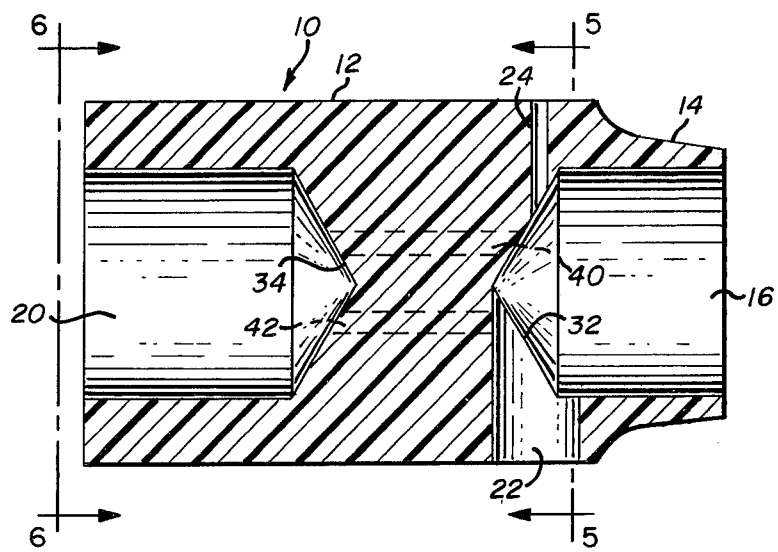
Fig_4
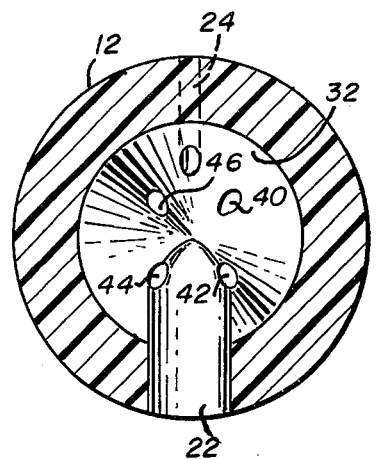
Fig_5
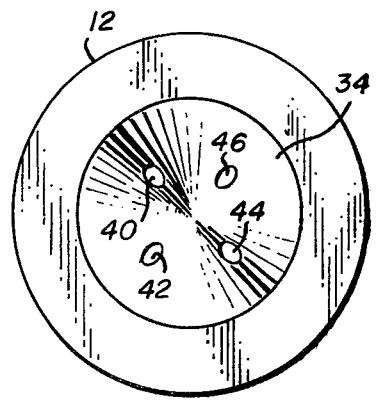
Fig_6

INHALATION DEVICE

FIELD OF THE INVENTION

This invention is related to devices for the administration of powdered medicaments by inhalation. More particularly, this invention relates to an inhalation device having, in the essential aspects thereof, no moving parts, yet which is capable of causing a powdered medicament, held within a container inserted into, or adjacent, the device, to be rapidly and effectively dispensed from the container, entrained in the air stream being inhaled and, thusly, carried into the nose, throat or lungs of the user where beneficial action of the medicament occurs.

BACKGROUND OF THE INVENTION

Known, prior art inhalation devices include, for example, those shown in U.S. Pat. Nos. 988,352; 2,507,702; and 2,603,216; and Great Britain Pat. No. 1,118,431.

SUMMARY OF THE INVENTION

The inhalation devices of the present invention include an elongate housing having one or more passageways for the passage of air therethrough, one end of the housing being adapted for insertion into the mouth or nose of a user. The passageway(s) extending through the housing terminate in an emptying chamber adjacent the output end of the housing. Means are provided adjacent the intersection of the passageway(s) with the emptying chamber for receiving or presenting a unit dose of powdered medicament for administration by inhalation. As shown, the housing has a port adapted to receive and hold a powdered medicament-holding container from which the medicament is to be entrained in the air stream passing through the device during inhalation. The container port can be slightly tilted (up to about 15° from the vertical) toward the passageway(s) (i.e., away from the output end of the housing) if desired.

In one embodiment, an air stream tube disposed opposite the means for holding the container extends close to, or into, the container and, during inhalation, directs a stream of air, into the container which assists in causing the powdered medicament to be expelled from the container during the inhalation process. This embodiment is shown in FIGS. 1–3, described in greater detail below.

In a second embodiment, a plurality of passageways extend through the device toward the emptying chamber, and the separate air stream tube is replaced with an integral tube-like passageway through which a stream of air is drawn into the medicament-holding container upon inhalation. This embodiment is shown in FIGS. 4–6, described in greater detail below.

Container, as used herein, is intended to include any means by which a unit dose of medicament is presented to the device for administration. Capsules are the presently preferred form of container; however, it is contemplated that other forms would be equally suitable if appropriate structural modifications of the device, to accommodate the different carrier, are made as, and if, necessary.

The container, in one aspect of the present invention, is manually opened, just prior to insertion into the device, to expose the medicament as is necessary for entrainment during inhalation. Optionally, in another aspect of this portion of the invention, the device can have means associated therewith for automatically opening the container as it is inserted into the device or means to open the container after it has been inserted into the device. In either case, such means eliminate the need to manually open the container prior to insertion, and, thusly, reduce the possibility of inadvertent spillage of the medicament prior to inhalation.

It has been found that, with the inhalation devices of this invention, the powdered medicament held within the container is rapidly and efficiently entrained in the air stream passing through the device during inhalation, and, as such, is carried into the nose, throat or lungs of the user where beneficial or therapeutic action of the medicament occurs.

BRIEF DESCRIPTION OF THE DRAWINGS

The foregoing and still further features and advantages of the present invention will become more apparent from the following detailed description, taken together with the accompanying drawings wherein:

FIG. 1 is a vertical cross-sectional view of one embodiment of an inhalation device of the present invention;

FIG. 2 is a cross-sectional view of the inhalation device of FIG. 1 taken along line 2—2 of FIG. 1;

FIG. 3 is an end view of the inhalation device of FIG. 1 taken along line 3—3 of FIG. 1;

FIG. 4 is a vertical cross-sectional view of an alternate embodiment of the inhalation device of the present invention;

FIG. 5 is a cross-sectional view of the inhalation device of FIG. 4 taken along line 5—5 of FIG. 4; and FIG. 6 is an end view of the inhalation device of FIG. 4 taken along line 6—6 of FIG. 4.

In the discussion below, reference will be made to a capsule as the exemplary container for presenting the medicament to the device for administration. As set forth above, other containers are contemplated for use with the devices of this invention.

Referring to FIG. 1, there is shown an inhalation device 10 having a substantially cylindrical elongate housing 12 (as can best be seen in FIGS. 2 and 3). At one end of housing 12 is a mouthpiece 14 intended for insertion into the mouth of a user thereof. Mouthpiece 14 can be redesigned to permit insertion into the nasal passages or, if desired, an adapter (not shown) can be placed over the mouthpiece to permit nasal use. Adjacent mouthpiece 14 is an emptying chamber 16 connected at the inner end thereof to passageway 18 which, in turn, is connected, at the end thereof remote from emptying chamber 16, to incoming or entrance chamber 20. Chamber 20 is an optional element of device 10 and can be eliminated if desired. Adjacent the lower, inner end of chamber 16, there is an opening or port 22 into which an opened capsule C, as shown in dotted outline in FIG. 1, is inserted prior to inhalation. Directly opposite port 22 there is a cylindrical passageway 24 in which there is inserted a hollow air stream tube 26 which extends from adjacent the surface 28 of housing 12 to about or below an extension of the longitudinal axis of passageway 18 and, preferably, to below the top 30 of opened capsule C. Optionally, the air stream tube can be integrally molded into the device thereby eliminating the need for a separate passageway 24. During inhalation, air drawn through air stream tube 26 is directed into the halfopened capsule and assists in causing the medicament to be expelled from the capsule. Slanted surfaces 32 and 34 connecting cylindrical chambers 16 and 20 with cylindrical passageway 18, respectively, are also shown in FIGS. 2 and 3. The manner of connecting passageway 18 with chambers 16 and 20 can be more squared-off or streamlined, as desired, as long as the particular configuration selected is effective to cause the powdered medicament to be expelled from the capsule, in the desired number of inhalations, during the inhalation, medicament-administering process.

A further embodiment of the inhalation devices of the present invention is shown in FIGS. 4–6 where like numerals as used in FIGS. 1–3 are utilized to represent like elements. Referring to FIGS. 4–6, the inhalation device shown therein has four passageways 40, 42, 44 and 46 extending longitudinally between incoming or entrance chamber 20 and emptying chamber 16. The four passageways are essentially at the corners of an imaginary square extending concentrically along the longitudinal axis of device 10 between chambers 20 and 16. However, it is contemplated that other configurations, including more or less passageways, would be suitable to provide the air flow through the device to cause the powdered medicament to be expelled from a medicament-holding capsule properly inserted into port 22 prior to inhalation.

In use, the patient manually opens the medicament-holding capsule or other medicament-holding container, and inserts the half-opened, medicament-holding portion thereof into port 22 essentially to the position shown in dotted outline in FIG. 1. The mouthpiece is then taken into the mouth and, upon inhalation, the air flowing through the device causes the medicament in the capsule to be entrained in the air stream flowing through emptying chamber 16. In this manner, the medicament is carried through the mouth and into the throat or lungs of the user where beneficial or therapeutic action of the medicament occurs.

As set forth above, means can be provided to automatically open the medicament-holding container upon insertion thereof into port 22, or means can be provided to open the medicament-holding container after it is inserted into the device. For example, a slide having a sharp cutting edge can be manually pushed against the top of the medicament-holding container, while held within the device, to slice open the top thereof and thereby expose the medicament to be administered. Or the air stream tube can have a sharp pointed bulbous lower edge which will, upon insertion of the container into the port, cut through the top of the container thereby exposing the medicament. Air will still be directed into the container through the center, hollow portion of the air stream tube during inhalation, while the powdered medicament will be expelled from the container through the annular space between the outside diameter of the air stream tube and the inner edge of the hole cut in the upper surface of the container by the bulbous lower edge of the tube, which is now sufficiently below the top of the container to permit expulsion of the powdered medicament. These means and other means equivalent thereto, which eliminate the need to manually open the container prior to insertion thereof into the inhalation device, are considered to be within the scope of this invention.

The entire device can be made of metal but preferably is made of suitable plastic material, such as nylon, polyacetal and polypropylene. The air stream tube can either be plastic, such as those referred to above, or a metal tube, such as, for example, a surgical needle, etc. With the exception of the capsule or other medicament-holding container, the device, in its basic elements, is preferably of unitary construction, although multipiece construction is contemplated, especially where means are provided to open the medicament-holding container. The potentially unitary design of the device of FIGS. 1–3 and the unitary design of the device of FIGS. 4–6 permit each device to be manufactured quite readily, thereby effecting substantial cost reduction in the manufacturing process, without adversely affecting medicament administration during inhalation.

The physical properties (i.e., flow characteristics) of each medicament formulation will affect the ease or manner in which it is dispensed with these or other inhalation devices. However, for a given powdered formulation, varying the diameter of passageway 18, the positioning of port 22 (from the position as shown toward the open end of chamber 16), the diameter of tube 26 or the distance it extends above or below the longitudinal axis of passageway 18 or the device, the tilt of the container opening toward passageway 18 and the depth to which the container is inserted into the opening, and/or, in general, the overall configuration and shape of chambers 16 and 20 and the passageway(s), devices can be designed to deliver the medicament in a different number of inhalations or in a longer or shorter period of time, depending upon the nasal or lung capacities of each particular user. Quite obviously, no single device will be suitable for all persons requiring administration of powdered medicaments since, for example, people with differing lung capacities are known to generate flow rates from about 30 liters/minute or so to about 120 liters/minute or so through inhalation devices of this and known types. Nonetheless, the devices of this invention afford such variability, through proper selection of the various design parameters, that a device, embraced within the scope of this invention, can be designed for a particular patient-generated flow rate to deliver the medicament according to a certain set of pre-determined objectives (e.g., slow or fast administration, one or more inhalations, etc.). The net result is that a family of devices, all embraced within the present invention, can be designed, each of which will deliver the medicament under a given set of selected administration conditions. Conversely, the devices of this invention can be designed to cover an extensive range of operating conditions, and thus be made suitable for use by a variety of persons having differing inhalation abilities or capacities.

While the present invention has been described with reference to specific embodiments thereof, it will be understood by those skilled in this art that various changes may be made and equivalents may be substituted without departing from the true spirit and scope of the invention. For example, as set forth above, the actual shape of the chambers 20 and 16 can be modified, as by streamlining, or, if desired, chamber 20 can be eliminated in toto; passageway 18 (and chamber 20) can be eliminated in toto; the longitudinal passageway or passageways can be replaced by radially extending passagesays, etc. Additionally, other modifications may be made to adapt a particular situation, material or composition of matter, structural desirability, or then-present objective to the spirit of this invention without departing from its essential teachings.

What is claimed is:

1. An inhalation device comprising an elongate housing having a passageway for the movement of air therethrough, one end of said housing being an output end adapted for insertion into the mouth or nasal passages of a user thereof; said passageway terminating in an emptying chamber adjacent the output end of said housing, the cross-sectional area of said passageway being less than the cross-sectional area of said emptying chamber; means for receiving a medicament-holding container; and hollow means for directing a stream of air drawn therethrough during inhalation into an open medicament-holding container positioned within said container receiving means, whereby air drawn through said passageway and through said hollow means cooperate to cause the medicament in the medicament-holding container to be dispensed therefrom.

2. The device of claim 1 wherein said container receiving means comprises a first opening in said housing adjacent said emptying chamber.

3. The device of claim 2 wherein said first opening is tilted toward said passageway at an angle up to about 15° from the vertical.

4. The device of claim 1 wherein the axis of said passageway lies along the longitudinal axis of said housing.

5. The device of claim 1 wherein said hollow means comprises a second opening in said housing and a hollow tube disposed therein, the tip of said hollow tube closest to said container receiving means extending below the longitudinal axis of said housing.

6. The device of claim 5 wherein said tip of said hollow tube extends into the medicament-holding container held by said container receiving means to a point above the level of the medicament but below the top of the container, the diameter of said hollow tube being less than the opening in the top of the container whereby, during inhalation, the medicament is dispensed from the container through the space defined by the outer surface of said hollow tube and the inner surface of the opening in the top of the container.

7. The device of claim 1 wherein said hollow means comprises a hollow tube-like passageway in said housing, the tip of said tube-like passageway closest to said first container receiving means extending below the longitudinal axis of said housing.

8. The device of claim 7 wherein said tip of said hollow tube-like passageway extends into the medicament-holding container held by said container receiving means to a point above the level of the medicament but below the top of the container, the diameter of said hollow tube-like passageway being less than the opening in the top of the container whereby, during inhalation, the medicament is dispensed from the container through the space defined by the outer surface of said hollow tube-like passageway and the inner surface of the opening in the top of the container.

9. The device of claim 1 wherein said emptying chamber and said passageway are substantially cylindrical.

10. The device of claim 1 wherein said container receiving means is closely adjacent the interface between said passageway and said emptying chamber.

11. The device of claim 1 wherein there are a plurality of passageways.

12. The device of claim 1 wherein there are four passageways.

13. An inhalation device comprising an elongate housing having a passageway for the movement of air therethrough, one end of said housing being an output end adapted for insertion into the mouth or nasal passages of a user thereof; said passageway connecting an entrance chamber and an emptying chamber adjacent the output end of said housing, the cross-sectional area of said passageway being less than the cross-sectional area of either said entrance chamber or said emptying chamber; a first opening in said housing adjacent said emptying chamber for receiving an open medicament-holding container; a second opening in said housing disposed opposite said first opening; and hollow means positioned within said second opening for directing a stream of air drawn therethrough during inhalation into an open medicament-holding container positioned within said first opening, whereby, during inhalation, air drawn through said passageway and through said hollow means cooperate to cause the medicament in the container to be dispensed therefrom.

14. The inhalation device of claim 13 wherein said hollow means comprises a hollow tube, the tip of which closest to said first opening extends below the longitudinal axis of said housing.

15. The inhalation device of claim 13 wherein said hollow means comprises a hollow tube, the tip of which closest to said first opening extends into the medicament-holding container held within said first opening to a point above the level of the medicament but below the top of the medicament-holding container, the diameter of said hollow tube being less than the opening in the top of the container whereby, during inhalation, the medicament is dispensed from the container through the space defined by the outer surface of said hollow tube and the inner surface of the opening in the top of the container.

16. The inhalation device of claim 13 wherein said hollow means comprises a hollow tube integral with said housing.

17. The device of claim 13 wherein said hollow means comprises a hollow tube not integral with said housing.

18. The device of claim 13 wherein said first opening is closely adjacent the interface between said passageway and said emptying chamber.

19. An inhalation device comprising an elongate housing having a plurality of passageways for the movement of air therethrough, one end of said housing being an output end adapted for insertion into the mouth or nasal passages of a user thereof; said passageways connecting an entrance chamber and an emptying chamber adjacent the output end of said housing, the aggregate cross-sectional area of said passageways being less than the cross-sectional area of either said entrance chamber or said emptying chamber; a first opening in said housing adjacent said emptying chamber for receiving a medicament-holding container; a second opening in said housing disposed opposite said first opening for directing a stream of air drawn therethrough during inhalation into an opened medicament-holding container positioned within said first opening, whereby, during inhalation, air drawn through said passageways and through said second opening cooperate to cause the medicament in the container to be dispensed therefrom.

20. The device of claim 19 wherein said second opening terminates above the longitudinal axis of said housing.

21. The device of claim 19 wherein said first opening is closely adjacent the interface between said passageways and said emptying chamber.

22. The device of claim 19 wherein there are four passageways positioned at the corners of an imaginary square concentrically along the longitudinal axis of said housing.

23. The device of claim 1 wherein said hollows means comprises a second opening in said housing and a hollow tube disposed therein, the tip of said hollow tube closest to said container receiving means extending to or above the longitudinal axis of said housing.

24. The device of claim 1 wherein said hollow means comprises a hollow tube-like passageway in said housing, the tip of said tube-like passageway closest to said first container receiving means extending to or above the longitudinal axis of said housing.

25. An inhalation device consisting of a housing having an output end adapted for insertion into the mouth or nasal passages of a user thereof; said housing having a hollow emptying chamber adjacent the output end thereof; means adjacent said emptying chamber for receiving a medicament-holding container; and hollow means for directing a concentrated stream of air drawn therethrough during inhalation into an open medicament-holding container positioned within said container receiving means, whereby air drawn through said hollow means during inhalation causes the medicament in the medicament-holding container to be dispensed therefrom.

26. The device of claim 25 wherein said container receiving means comprises a first opening in said housing adjacent said emptying chamber, said first opening being tilted away from said output end at an angle up to about 15° from the vertical.

27. The device of claim 25 wherein said hollow means comprises a second opening in said housing and a hollow tube disposed therein.

28. The device of claim 25 wherein said hollow means comprises a hollow tube-like passageway in said housing.

* * * * *